(12) United States Patent
Williams et al.

(10) Patent No.: US 11,839,378 B2
(45) Date of Patent: Dec. 12, 2023

(54) CIRCULAR STAPLING INSTRUMENTS

(71) Applicant: Covidien LP, Mansfield, MA (US)

(72) Inventors: Justin Williams, Southbury, CT (US); Patrick Mozdzierz, Glastonbury, CT (US); Ramiro Cabrera, Cheshire, CT (US); Christopher Penna, Guilford, CT (US); Joseph Eisinger, Northford, CT (US); Joseph Guerrera, Watertown, CT (US); Steven Joyce, Durham, CT (US)

(73) Assignee: Covidien LP, Mansfield, MA (US)

( * ) Notice: Subject to any disclaimer, the term of this patent is extended or adjusted under 35 U.S.C. 154(b) by 659 days.

(21) Appl. No.: 16/824,156

(22) Filed: Mar. 19, 2020

(65) Prior Publication Data

US 2020/0330098 A1 Oct. 22, 2020

Related U.S. Application Data

(60) Provisional application No. 62/836,250, filed on Apr. 19, 2019.

(51) Int. Cl.
*A61B 17/115* (2006.01)
*A61B 17/00* (2006.01)
*A61B 17/072* (2006.01)

(52) U.S. Cl.
CPC . *A61B 17/1155* (2013.01); *A61B 2017/00486* (2013.01); *A61B 2017/07271* (2013.01); *A61B 2017/07285* (2013.01)

(58) Field of Classification Search
CPC .......... A61B 2017/07271; A61B 2017/07285; A61B 2017/00486; A61B 17/1155
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |

(Continued)

FOREIGN PATENT DOCUMENTS

| | | |
|---|---|---|
| CA | 908529 A | 8/1972 |
| CA | 2805365 A1 | 8/2013 |

(Continued)

*Primary Examiner* — Anna K Kinsaul
*Assistant Examiner* — Himchan Song
(74) *Attorney, Agent, or Firm* — CARTER, DELUCA & FARRELL LLP (57) ABSTRACT

Apparatus and methods for improved tissue cutting of circular stapling instruments include a cartridge assembly configured to maximize the force during a cutting stroke. In embodiments, the cartridge assembly is configured to maintain engagement between a knife assembly and a drive member during retraction of the knife. Alternatively, or in addition, the cartridge assembly is configured to prevent incidental advancement of the knife assembly.

9 Claims, 9 Drawing Sheets

(56) References Cited

U.S. PATENT DOCUMENTS

| | | |
|---|---|---|
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant ............ A61B 17/115 227/19 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A * | 11/1995 | Chen ............ A61B 17/1114 606/154 |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 * | 7/2001 | Balazs ............ A61B 17/072 606/139 |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |

(56) References Cited

U.S. PATENT DOCUMENTS

| | | |
|---|---|---|
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0150965 A1* | 6/2017 | Williams ........... A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

CIRCULAR STAPLING INSTRUMENTS

CROSS-REFERENCE TO RELATED APPLICATIONS

This application claims the benefit of and priority to U.S. Provisional Patent Application Ser. No. 62/836,250 filed Apr. 19, 2019, the entire disclosure of which is incorporated by reference herein.

BACKGROUND

Technical Field

The present disclosure relates to circular stapling instruments. More particularly, the present disclosure relates to a circular stapling instrument having an independent cutting stroke.

Background of Related Art

Circular stapling instruments are known, as are their use in closed procedures, i.e., endoscopic, laparoscopic or through natural body orifices. Typically the circular stapling instruments include a cartridge assembly on a distal end of an elongate body. The cartridge assembly includes a mechanism for forming staples and a knife for cutting the stapled tissue.

Typically, tissue is stapled during a first or stapling stroke of the circular stapling instrument, and the stapled tissue is subsequently cut during a second or cutting stroke. During the cutting stroke, a circular knife is advanced through the stapled tissue. The greater the force acting on the knife during the cutting stroke, the cleaner and more effective the cut. Following the cutting stroke, retraction of the knife is important to prevent incidental contact of the knife with the patient, the user, and operating room support staff.

Therefore, it would be beneficial to have a circular stapling instrument including a cartridge assembly configured to maximize the force during a cutting stroke. It would also be beneficial to have a circular stapling instrument including a cartridge assembly configured to maintain engagement between a knife assembly and a drive member during retraction of the knife, and to prevent incidental advancement of the knife assembly.

SUMMARY

Accordingly, a circular stapling instrument having a cartridge assembly configured to maximize the force during a cutting stroke is provided. The circular stapling instrument includes a handle assembly and an elongate body extending from the handle assembly and including a drive member. A cartridge assembly is mounted on a distal end of the elongate body. The cartridge assembly includes a knife assembly and an outer housing. The knife assembly is secured to the outer housing by a breakable connection. A drive assembly extends from the elongate body and is operably disposed between the drive member and the knife assembly. The drive assembly includes a proximal drive section, a distal drive section, and a biasing member disposed between the proximal and distal drive sections. Advancement of the proximal drive section a first distance compresses the biasing member, and advancement of the proximal drive section a second distance breaks the connection between the knife assembly and the outer housing.

In embodiments, the breakable connection maintains the knife assembly in a retracted position and upon breaking of the breakable connection, the biasing member advances the distal drive section distally to advance the knife assembly. Compressing the biasing member may store energy in the biasing member. The biasing member may release the stored energy when the breakable connection breaks. The biasing member may be a coil spring. The breakable connection may be a weld.

The knife assembly may include a knife carrier and a knife secured to the carrier. The proximal and distal drive sections may be tubular. The proximal and distal drive sections and the biasing member may be coaxial.

Also provided is a cartridge assembly for a circular stapling instrument configured to maintain engagement between a knife assembly and a drive member during retraction of the knife assembly. The cartridge assembly includes a housing having an outer cylindrical portion and an inner cylindrical portion and defines a recess therebetween. The inner cylindrical portion defines a plurality of longitudinally extending grooves and includes a plurality of elongate detents disposed distally of the plurality of longitudinally extending grooves. The cartridge assembly further includes a knife assembly received within the recess and moveable between a retracted position and an advanced position. The knife assembly includes a knife carrier received about the inner cylindrical portion. The knife carrier includes a plurality of radially inward extending protrusions received within the plurality of longitudinal grooves when the knife assembly is in the retracted position and disposed outward of the elongate detent when the knife assembly is advanced from the retracted position.

In embodiments, engagement between the plurality of protrusions and the plurality of elongate detents retains the knife assembly in the retracted position. The protrusions may remain in contact with the elongate detents as the knife assembly moves from the retracted position to the advanced position. The knife assembly may be substantially cylindrical.

Also provided is a method of performing a surgical stapling procedure. The method includes advancing a drive member of a circular stapling instrument a first distance to engage a knife assembly disposed in an initial position within a cartridge assembly of the circular stapling instrument. The drive member is then advanced a second distance to advance the knife assembly from the initial position and then retracted the second distance to return the knife assembly to the initial position. A trocar member is advanced to permit separation of an anvil assembly from the circular stapling instrument. Subsequent to advancing the trocar member, the drive member is retracted the first distance to disengage the drive member from the knife assembly.

In embodiments, the method further includes advancing a pusher assembly to staple tissue disposed between the cartridge assembly and the anvil assembly. The method may further include separating the cartridge assembly from an adapter assembly of the circular stapling instrument, separating the anvil assembly from the trocar member, and/or retracting the trocar member subsequent to separating the anvil assembly from the circular stapling instrument. Advancing the drive member the second distance may cause the cutting of tissue disposed between the anvil assembly and the cartridge assembly.

DESCRIPTION OF THE DRAWINGS

An embodiment of a circular stapling instrument including a cartridge assembly that is actuated independently from actuation of the cutting assembly is disclosed herein with reference to the drawings, wherein.

DETAILED DESCRIPTION

Embodiments of the presently disclosed cartridge assemblies for circular stapling instruments will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 1:
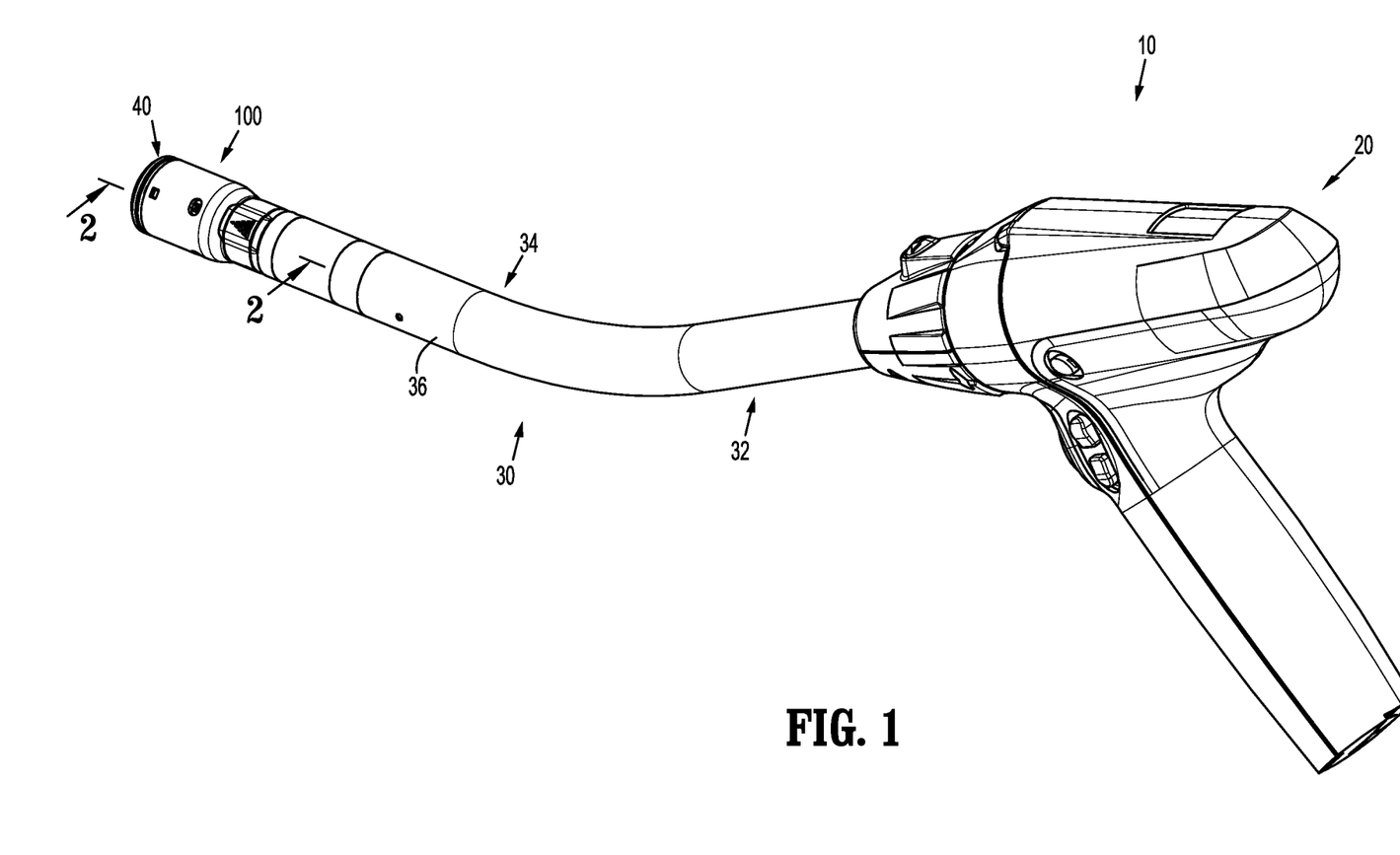
FIG. 1 is a perspective view of a circular stapling instrument including a cartridge assembly according to an embodiment of the present disclosure.

Referring initially to FIG. 1, a cartridge assembly according to an embodiment of the present disclosure, shown generally as cartridge assembly 100, is a component of a circular stapling instrument 10. The circular stapling instrument 10 further includes a powered and programmable handle assembly 20, an adapter assembly 30 releasably secured to the handle assembly 20, and an anvil assembly 40 releasably secured to a trocar assembly 50 (FIG. 2) extending from the adapter assembly 30. Although shown and described with reference to the circular stapling instrument 10, it is envisioned that the aspects of the present disclosure may be modified for use with manual circular stapling instruments having various configurations, and with powered surgical stapling instruments having alternative configurations. For a detailed description of exemplary powered handle assemblies for circular stapling instruments, please refer to commonly owned U.S. Pat. Nos. 9,023,014 and 9,055,943 ("the '014 patent" and "the '943 patent", respectively), the content of each of which is incorporated by reference herein in its entirety.

With continued reference to FIG. 1, the adapter assembly 30 includes a proximal portion 32 configured for operable connection to the handle assembly 20 (FIG. 1) and a distal portion 34 configured for operable connection to the cartridge assembly 100 and to the anvil assembly 40 (FIG. 1). Although shown and described as forming an integral unit, it is envisioned that the proximal and distal portions 32, 34 may be formed as separate units that are releasably securable to one another. The adapter assembly 30 will only be described to the extent necessary to fully disclose the aspects of the present disclosure. For a detailed description of an exemplary adapter assembly, please refer to commonly owned U.S. Pat. App. Pub. No. 2016/0106406 ("the '406 Publication"), the content of which is incorporated by reference herein in its entirety.

The adapter assembly 30 includes an outer sleeve 36, and a connector housing 38 secured to a distal end of the outer sleeve 36. The connector housing 38 is configured to releasably secure cartridge assembly 100 to the adapter assembly 30.

Figure 2:
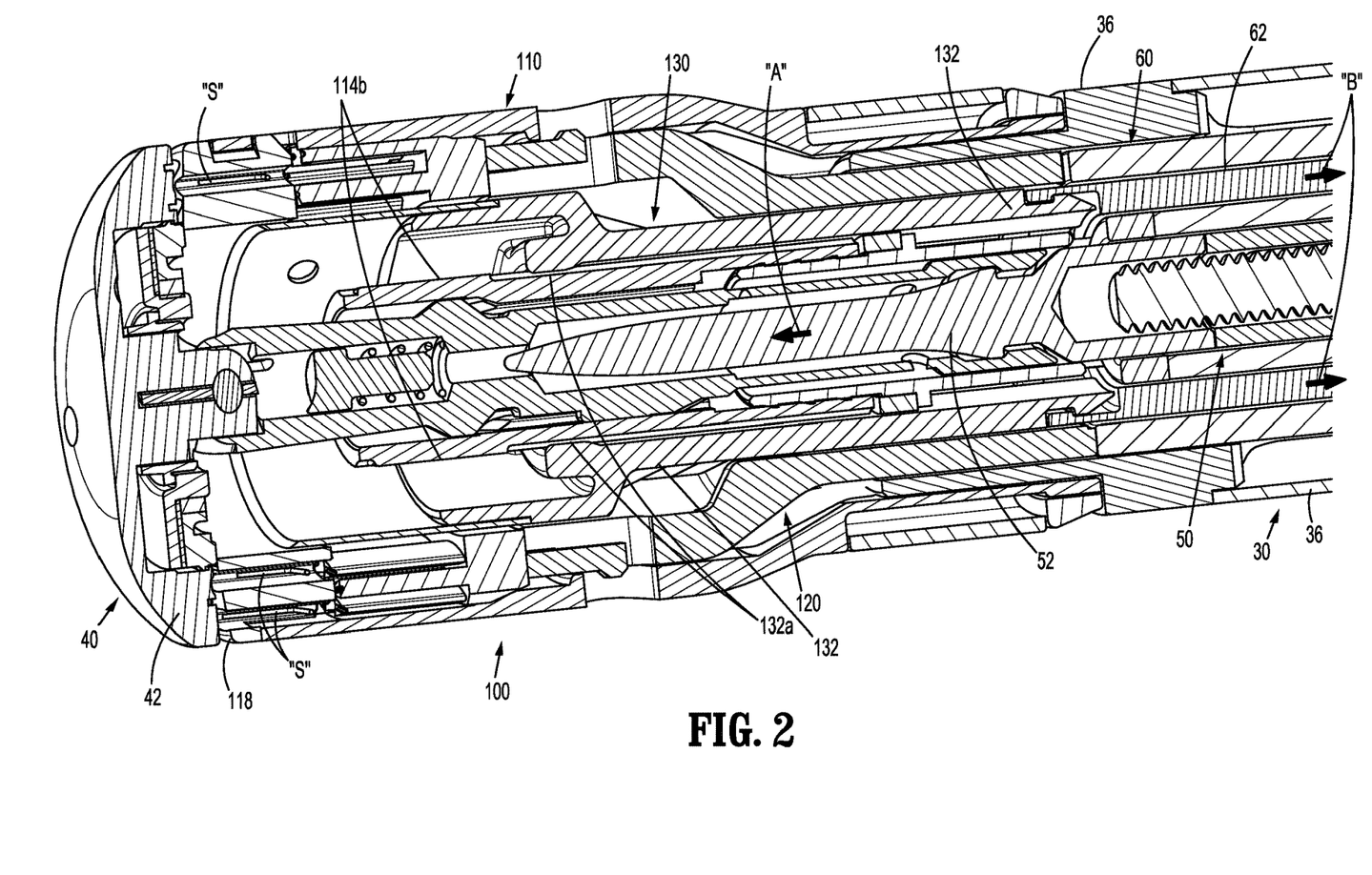
FIG. 2 is an enlarged, cross-sectional view of the cartridge assembly of the circular stapling instrument of FIG. 1, taken along ling 2-2 shown in FIG. 1.

Turning to FIG. 2, the cartridge assembly 100 of the surgical stapling instrument 10 (FIG. 1) is operably mounted to a distal end of the adapter assembly 30 (FIG. 1). The cartridge assembly 100 includes an outer housing or shell member 110, a staple pusher assembly 120, and a knife assembly 130. The staple pusher assembly 120 and the knife assembly 130 are operably disposed within the outer housing 110. The cartridge assembly 100 will only be described to the extent necessary to fully disclose the aspects of the present disclosure. For a detailed description of the structure and function of exemplary cartridge assemblies, please refer to commonly owned U.S. Pat. Nos. 9,038,882 and 9,168,042 ("the '882 patent" and "the '042 patent", respectively), the content of each of which is incorporated herein in its entirety.

With continued reference to FIG. 2, the trocar assembly 50 extends from the adapter assembly 30 through the cartridge assembly 100 when the cartridge assembly 100 is secured to the adapter assembly 30. The anvil assembly 40 is releasably secured to a trocar member 52 of the trocar assembly 50. Please refer to the '882 and '042 patents for detailed description of exemplary trocar assemblies.

Figure 3:
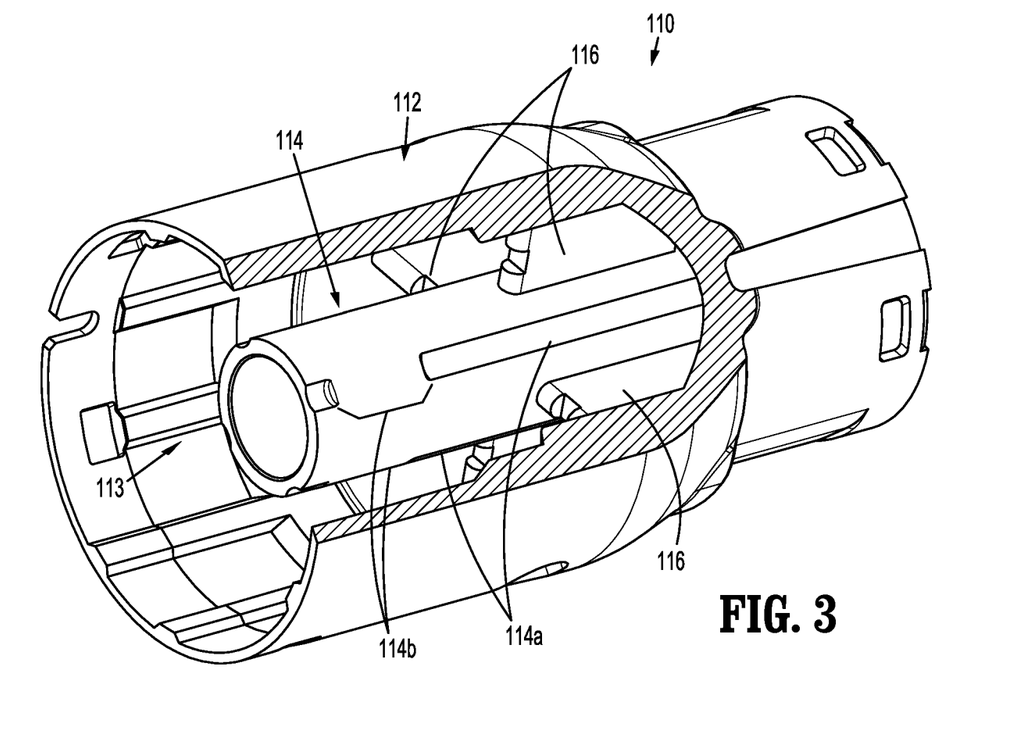
FIG. 3 is a side, perspective view of an outer housing of the cartridge assembly of FIG. 1.

With additional reference to FIG. 3, the outer housing 110 of the cartridge assembly 100 includes an outer cylindrical portion 112, an inner cylindrical portion 114, and a plurality of radially extending supports or ribs 116 extending between and interconnecting the outer and inner cylindrical portions 112, 114. The outer cylindrical portion 112 and the inner cylindrical portion 114 are coaxial and define a recess 113 therebetween configured to operably receive the staple pusher assembly 120 (FIG. 2) and the knife assembly 130 (FIG. 3).

The inner cylindrical portion 114 of the outer housing 110 defines a plurality of longitudinal grooves 114a extending longitudinally along an outer surface thereof. Each of the longitudinal grooves 114a includes an elongate detent 114b. As will be described in further detail below, the longitudinal grooves 114a are configured to receive protrusions 132a extending from an inner surface of a knife carrier 132 (FIG. 4) of the knife assembly 130. The elongate detents 114b extend along a distal portion of the inner cylindrical portion 114 of the outer housing 110 and inhibit advancement of the knife carrier 132 of knife assembly 130 during a first or staple forming stroke of circular stapling instrument 10, and prior to advancement of a second drive member 62. As will also be described in further detail below, the elongate detents 114b operate to reduce the force required retract the knife assembly 130 following the cutting stroke.

With continued reference to FIG. 2, the staple pusher assembly 120 is operably received within the recess 113 of the outer housing 110 and is releasably secured to a first drive member 60 extending from the adapter assembly 30 of the surgical stapling instrument 10. Advancement of the first drive member 60 advances the staple pusher assembly 120 to eject staples "S" from within a staple cartridge 118 of the cartridge assembly 100 and into an anvil member 42 of the anvil assembly 40 to staple tissue (not shown) disposed between the anvil member 42 and the staple cartridge 118.

The knife assembly 130 is operably received within the staple pusher assembly 120 and about the inner cylindrical portion 114 of the outer housing 110. The knife assembly 130 is releasably secured to the second drive member 62 extending from the adapter assembly 30. Advancement of the second drive member 62 advances the knife assembly 130 to cut the stapled tissue (not shown) disposed between the anvil member 42 and the staple cartridge 118. It is envisioned that the first and second drive members 60, 62 may be advanced simultaneously or sequentially.

Figure 4:
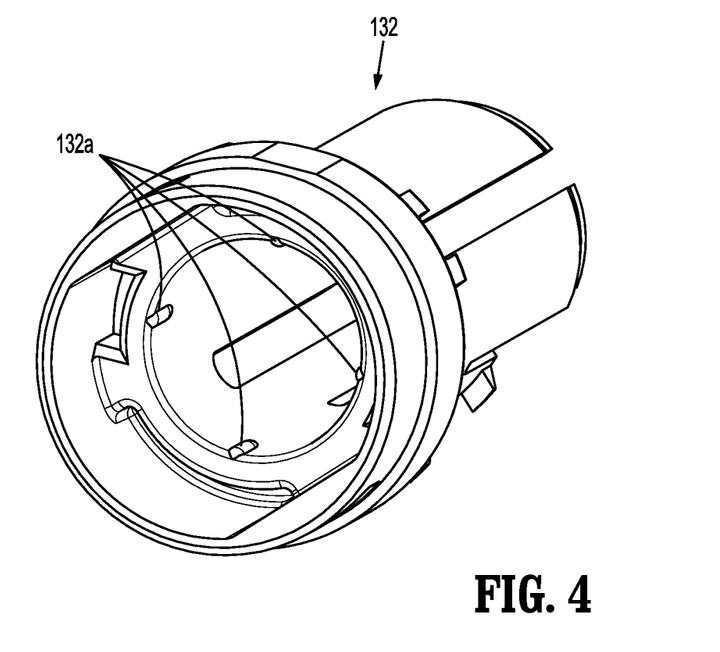
FIG. 4 is end, perspective view of a knife carrier of the cartridge assembly of FIG. 1.

With additional reference to FIG. 4, the knife assembly 130 includes a knife carrier 132. The knife carrier 132 supports a knife 134 (FIG. 2) and is slidingly received about the inner cylindrical portion 114 of the outer housing 110. The protrusions 132a of the knife carrier 132 extend from an inner surface of the knife carrier 132 and are configured for receipt within the longitudinal grooves 114a in the inner cylindrical portion 114 when the knife assembly 130 is in a retracted position. Engagement of the protrusions 132a of the knife carrier 132 with the elongate detents 114b of the inner cylindrical portion 114 of the outer housing 110 prevents advancement of the knife assembly 130 prior to advancement of a second drive member 62, e.g., during shipping and/or during the staple forming stroke of circular stapling instrument 10.

Figure 5:
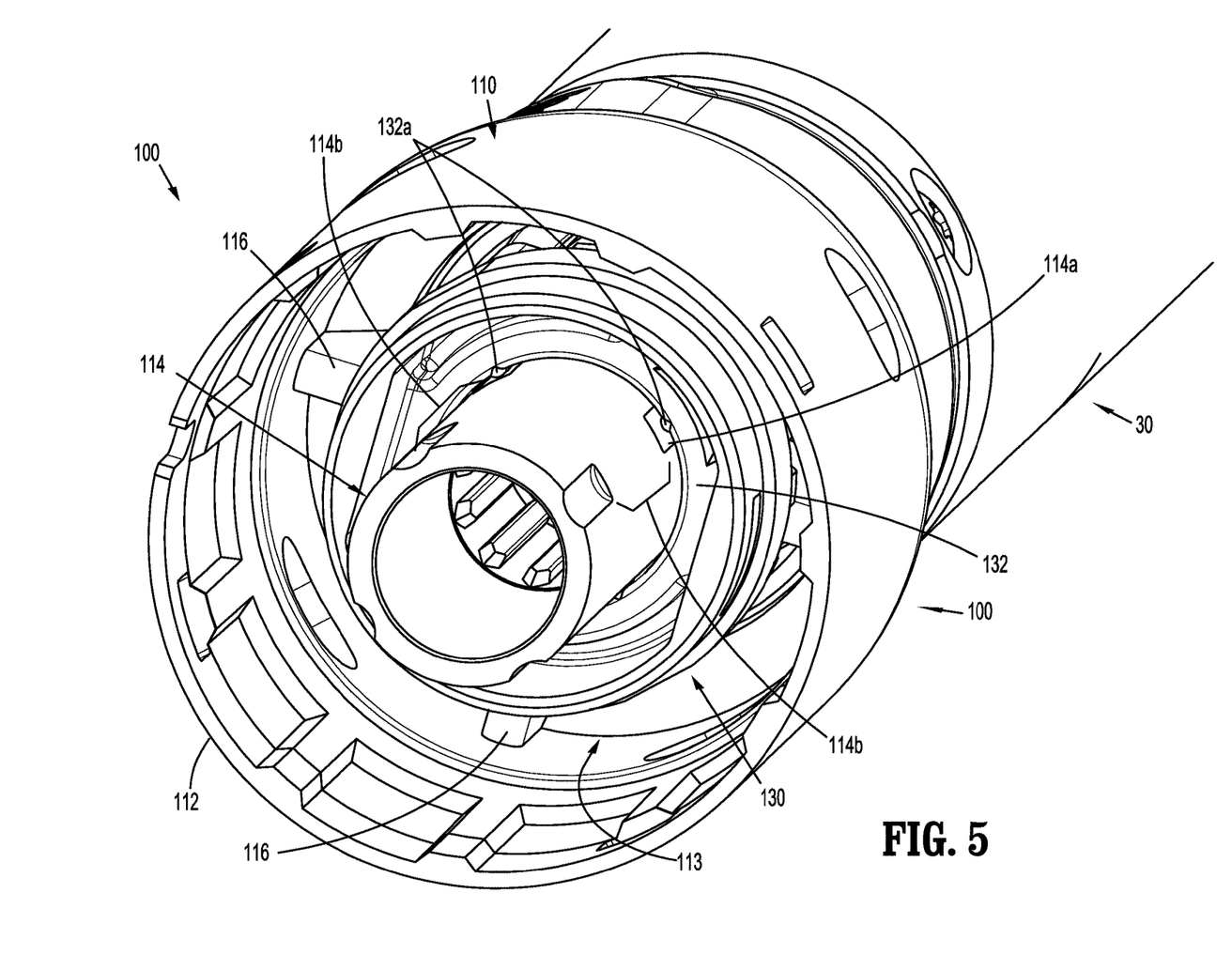
FIG. 5 is an end, perspective view of the knife carrier of FIG. 4 received within the outer housing of FIG. 3.

More particularly, and as shown in FIG. 5, the protrusions 132a of the knife carrier 132 of the knife assembly 130 are received within the longitudinal grooves 114a in the inner cylindrical portion 114 of the outer housing 110. During a cutting stroke of the circular stapling instrument 10 (FIG. 1), the second drive member 62 provides a pushing force on the knife carrier 132 of the knife assembly 130 that causes the protrusions 132a of the knife carrier 132 to come into contact with and move radially outward of the elongate detents 114b of the outer housing 110 to permit advancement of the knife carrier 132 within the outer housing 110. The elongate detents 114b have a length that is at least as long as a length of the cutting stroke of the knife assembly 130. By extending the detents 114b of the inner cylindrical portion 114 of the outer housing 110 and eliminating longitudinal grooves on distal ends of the detents 114b, the protrusions 132a of the knife carrier 132 remain in contact with and are disposed radially outward of the elongate detents 114b throughout the advancing and retracting portions of the cutting stroke of the knife assembly 130. In this manner, the force required to retract the knife carrier 132 during the cutting stroke of the circular stapling instrument 10 remains constant through the cutting stroke.

In operation, during the advancing portion of the cutting stroke of the surgical stapling instrument 10, a force is applied to the knife carrier 132 of the knife assembly 130 by the second drive member 62. The force supplied by the second drive member 62 is sufficient to overcome the engagement between the protrusions 132a of the knife carrier 132 and the elongate detent 114b of the inner cylindrical portion 114 of the outer housing 110. Once a sufficient force is achieved within the knife assembly 130, the protrusions 132a of the knife carrier 132 are moved from within the longitudinal grooves 114a of the inner cylindrical portion 114 of the outer housing 110 into contact with and radially outward of the elongate detent 114b as the knife carrier 132 moves distally over the inner cylindrical portion 114 of the outer housing 110.

As noted above, during the advancing portion of the cutting stroke of the circular stapling instrument 10, the protrusions 132a of the knife carrier 132 remain in contact with the elongate detent 114b of the inner cylindrical portion 114 of the outer housing 110. During the retracting portion of the cutting stroke, the protrusions 132a of the knife carrier 132 continue to remain in contact with and radially outward of the elongate detents 114b until the knife carrier 132 is retracted to its initial position, at which point, the protrusions 132a are returned to the longitudinal grooves 114a. The elongate detents 114b then again prevent advancement of the knife assembly 130, e.g., act as a stop, to retain the knife assembly 130 in its retracted position and prevent the knife carrier 132 from advancing and exposing the knife 134.

By maintaining the protrusions 132a of the knife carrier 132 in constant contact with the elongate detent 114b of the inner cylindrical portion 114 of the outer housing 110 throughout the cutting stroke of the circular stapling instrument 10, no additional force is required to engage the protrusions 132a with the elongate detents 114b during retraction of the knife carrier 132 as the protrusions 132a are engaged with the elongate detents 114b. Thus, unlike during the advancing portion of the cutting stroke, when an increased force on the knife carrier 132 is required to move the protrusions 132a of the knife carrier 132 into contact with and about the elongate detents 114b to permit the advancement of the knife carrier 132, the knife carrier 132 may be retracted without any additional force, thereby reducing the possibility that the knife carrier 132 may become separated from the second drive member 62 prior to complete retraction of the knife carrier 132.

As noted above, once the knife carrier 132 of the knife assembly 130 is returned toits retracted position, the elongate detents 114b of the inner cylindrical portion 114 of the outer housing 110 operate to retain the knife assembly 130 in the retracted position. Continued retraction of the second drive member 62 disengages the second drive member 62 from the knife carrier 132 such that the cartridge assembly 100 may be separated from the adapter assembly 30 (FIG. 1) to permit replacement of the cartridge assembly 100.

The operation of the circular stapling instrument 10 is controlled by the powered handle assembly 20 (FIG. 1). More particularly, the powered handle assembly 20 is programmed to advance the staple pusher assembly 120 (FIG. 2) during a staple forming stroke of the circular stapling instrument 10 (FIG. 1), and to subsequently advance the knife assembly 130 during the cutting stroke. As noted above, following the cutting stroke, the knife assembly 130 is retracted to prevent incidental contact of the patient, user, or other medical staff with the knife 132.

Typically, the powered handle assembly 20 is programmed to retract the second drive member 62 to return the knife assembly 130 to its initial position, and continue retracting the second drive member 62 to disengage the second drive member 62 from the knife carrier 132 to permit separation of the cartridge assembly 100 from the adapter assembly 30 (FIG. 1). Once the second drive member 62 disengages from the knife carrier 132, the protrusions 132a of the knife carrier 132 of the knife assembly 130 engage the elongate detents 114b of the inner cylindrical portion 114 of the outer housing 110 to retain the knife assembly 130 in its retracted position, and thereby prevent exposing the knife 134.

Separation of the cartridge assembly 100 from the adapter assembly 30 further requires advancing the trocar member 52 (FIG. 2) to advance the anvil assembly 40 (FIG. 2) to permit separation of the anvil assembly 40 from the trocar member 52. Generally, the trocar member 52 is advanced subsequent to retraction of the knife assembly 130 and separation of the knife assembly 130 from the second drive member 62. In this manner, the knife assembly 130 is retained in its retracted position solely through engagement of the protrusions 132a of the knife carrier 132 with the elongate detents 114b of the inner cylindrical portion 114. In the unlikely event the knife assembly 130 experiences a force sufficient to overcome the engagement of the protrusions 132a of the knife carrier 132 with the elongate detents 114b of the inner cylindrical portion 114, e.g., as the trocar member 52 (FIG. 2) of the trocar assembly 50 is advanced to facilitate separation of the anvil assembly 40 (FIG. 2) from the trocar member 52, as indicated by arrows "A" in FIG. 2, the knife 134 of the knife assembly 130 may become exposed.

To reduce the likelihood that the knife assembly 130 may be accidently re-advanced prior to separation of the cartridge assembly 100 from the adapter assembly 30, and thereby expose the knife 134, in embodiments, the powered handle assembly 20 (FIG. 1) is programmed to initially retract the second drive member 62, as indicated by arrows "B" in FIG. 2, a first distance sufficient to return the knife assembly 130 to its initial position, e.g., so that the protrusions 132a of the knife carrier 132 are received within the longitudinal grooves 114a and reengage the elongate detent 114b of the inner cylindrical portion 114 of the outer housing 110, but not enough to disengage the second drive member 62 from the knife carrier 132. The powered handle assembly 20 is programmed to maintain the second drive member 62 in this partially retracted position until the anvil assembly 40 (FIG. 2) is separated from the trocar member 52 (FIG. 2), e.g., the trocar member 52 is advanced, as indicated by arrow "B" in FIG. 2. In this manner, the second drive member 62 facilitates retention of the knife assembly 130 in its initial position, and thereby reduces the likelihood that the knife 134 will become exposed prior to separation of the cartridge assembly 100 from the adapter assembly 30.

Following separation of the anvil assembly 40 (FIG. 2) from the trocar assembly 52 (FIG. 2), the powered handle assembly 20 is further programmed to complete the retraction of the second drive member 62, as indicated by arrows "B" to cause the second drive member 62 to disengage from the knife assembly 130.

With reference now to FIGS. 6-11, another cartridge assembly according to an embodiment of the present disclosure is shown generally as cartridge assembly 200. The cartridge assembly 200 is substantially similar to the cartridge assembly 100 described hereinabove, and will only be described in detail as relates to the differences therebetween. As will be described in further detail below, the cartridge assembly 200 is configured to provide a cleaner and less traumatic cutting stroke.

Figure 6:
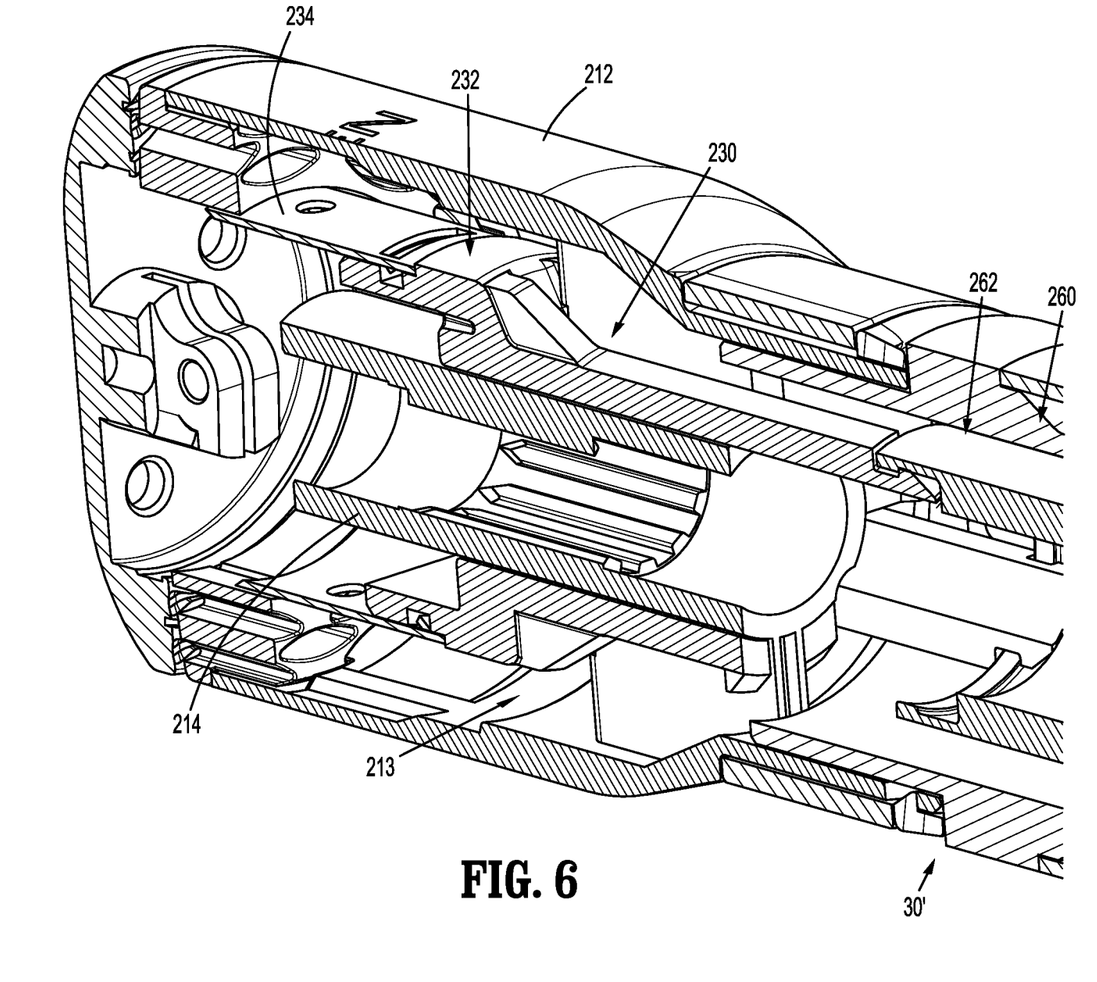
FIG. 6 is a cross-sectional side, perspective view of a cartridge assembly according to another embodiment of the present disclosure.

With particular reference to FIG. 6, the cartridge assembly 200 includes a knife assembly 230 disposed within a recess 213 between an outer cylindrical portion 212 and an inner cylindrical portion 214 of an outer housing 210 of the cartridge assembly 200. A knife carrier 232 of the knife assembly 230 is releasably secured, e.g., breakable connection, to the inner cylindrical portion 214 of the outer housing 210 of the cartridge assembly 200. In embodiments, the knife carrier 232 is spot welded to the inner cylindrical portion 214 of the outer housing 210. Alternatively, the knife carrier 232 may be secured relative to the inner cylindrical portion 214 of the outer housing 210 with one or more mechanical fasteners, a frangible connection, or in any other releasable manner.

A drive assembly 260 is operably supported within a distal end of adapter assembly 30'. The drive assembly 260 operably engages the knife assembly 230 of the cartridge assembly 200 and is configured to increase the velocity at which a knife 234 of the knife assembly 230 contacts tissue during a cutting stroke of the circular stapling instrument 10. More particularly, and as will described in further detail below, the drive assembly 260 is disposed between a drive member (not shown) of the circular stapling instrument 10 and the knife assembly 230 of the cartridge assembly 200. During a first portion of the cutting stroke energy is stored within the drive assembly 260. Once a force sufficient to separate the connection, e.g., weld, between the knife carrier 232 of the knife assembly 230 and the inner cylindrical portion 214 of the outer housing 210 is achieved, the knife carrier 232 separates from the inner cylindrical portion 214 and the stored energy in the drive assembly 260 is released, thereby instantaneously advancing the knife assembly 230. In this manner, the knife assembly 230 is advanced with a higher velocity than if the knife assembly 230 was advanced continuously throughout the cutting stroke.

Figure 7:
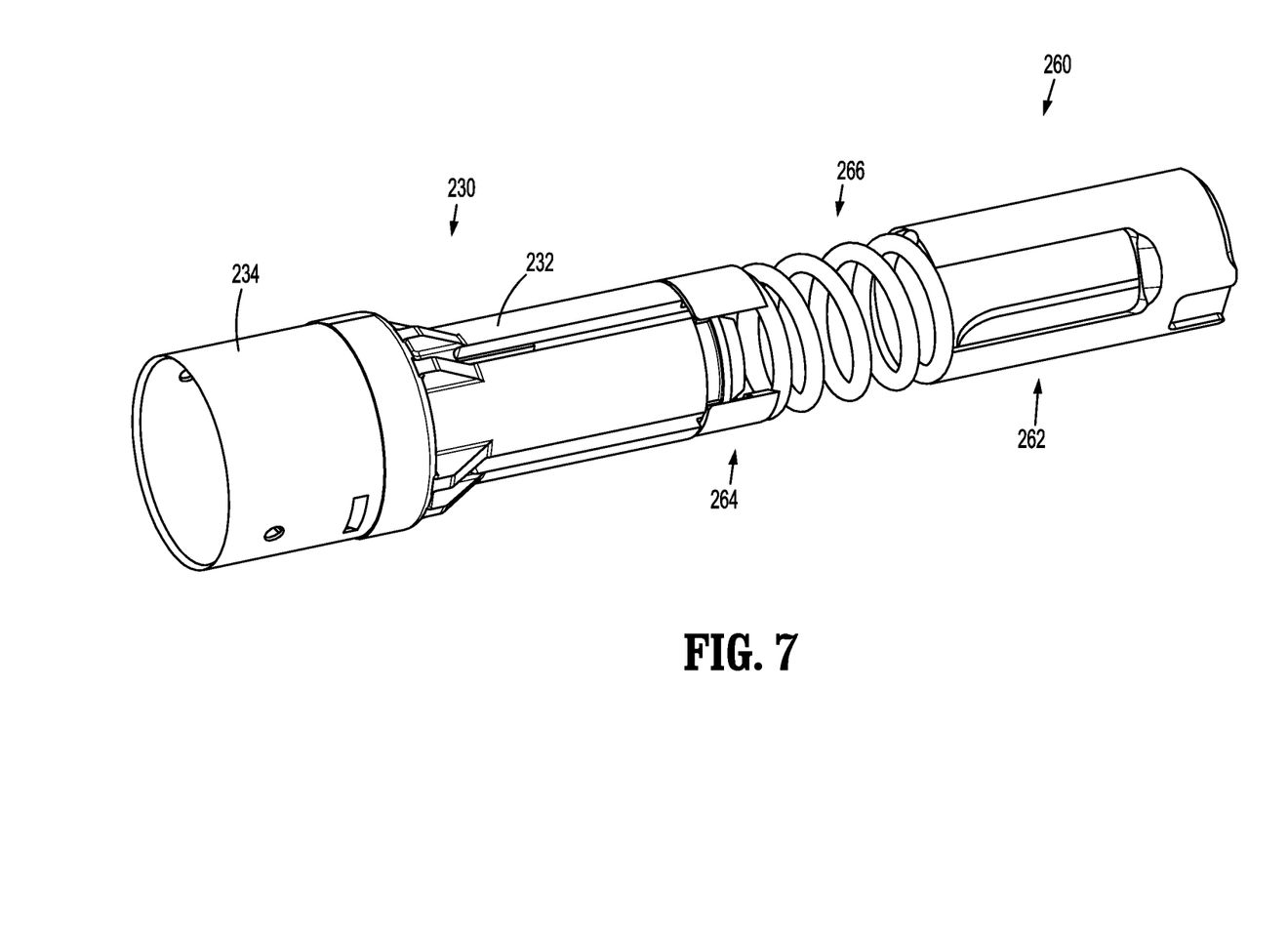
FIG. 7 is a side, perspective view of a knife assembly and a drive assembly of the cartridge assembly of FIG. 6.
Figure 8:
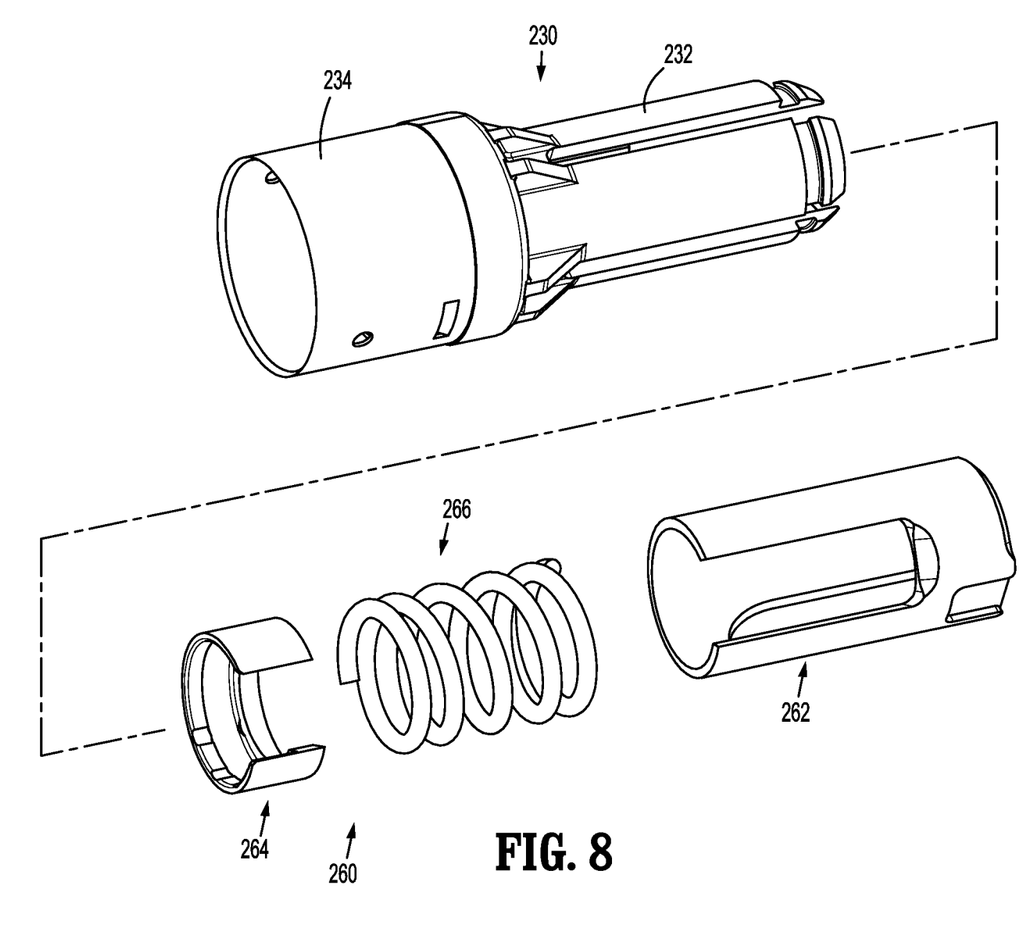
FIG. 8 is an exploded side, perspective view of the knife assembly and the drive assembly of FIG. 7.
Figure 9:
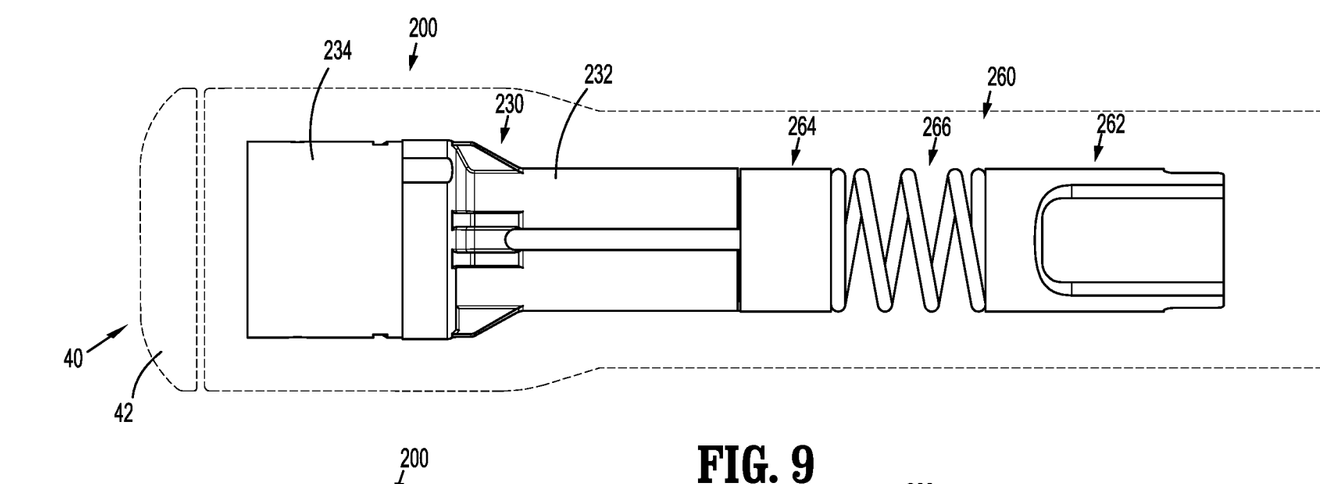
FIG. 9 is a side view of the knife assembly and the drive assembly of FIG. 7, with the knife assembly in a retracted position and the drive assembly in an initial condition.

With reference to FIGS. 7-9, the drive assembly 260 includes a proximal drive section 262 configured for operable connection with a drive member (not shown), a distal drive section 264 configured for operable connection with a knife carrier 232 of the knife assembly 230 of the cartridge assembly 200, and a biasing member 266 disposed between the proximal and distal drive sections 262, 264. As shown, the biasing member 266 of the drive assembly 260 includes a coil spring 266. The coil spring 266 may be formed of metal, plastic, or other suitable material. The coil spring 266a may be secured to the proximal and distal drive sections 262, 264 with welding, adhesive, mechanical fasteners, or in any other suitable manner. In embodiments, and as shown, the proximal and distal drive sections 262, 264, and the biasing member 266 are coaxial.

Figure 10:
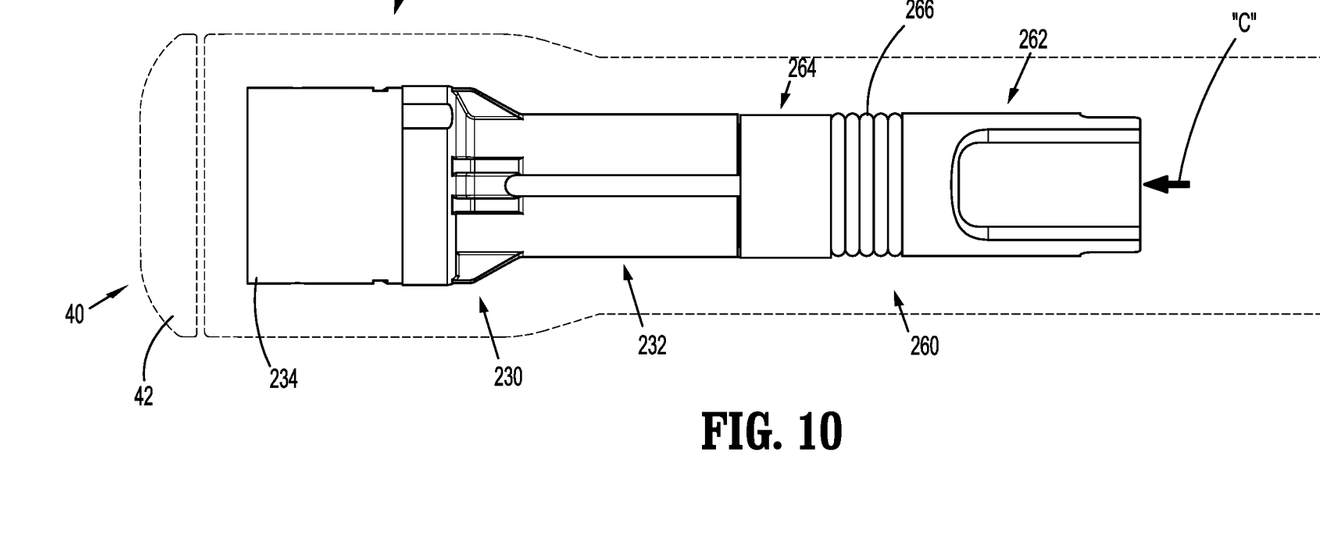
FIG. 10 is a side view of the knife assembly and the drive assembly of FIG. 7, with the knife assembly in the retracted position and the drive assembly in a loaded condition.

As shown in FIG. 10, advancement of the proximal drive section 262, as indicated by arrow "C", without corresponding advancement of the distal drive section 264, causes compression of the biasing member 266. As noted above, the distal drive section 264 is in engagement with the knife carrier 232 of the knife assembly 230, and the knife carrier 232 is fixed, e.g., welded, to the inner cylindrical portion 214 of the outer housing 210 of the cartridge assembly 200. As the biasing member 266 is compressed, energy is stored in the biasing member 266.

Figure 11:
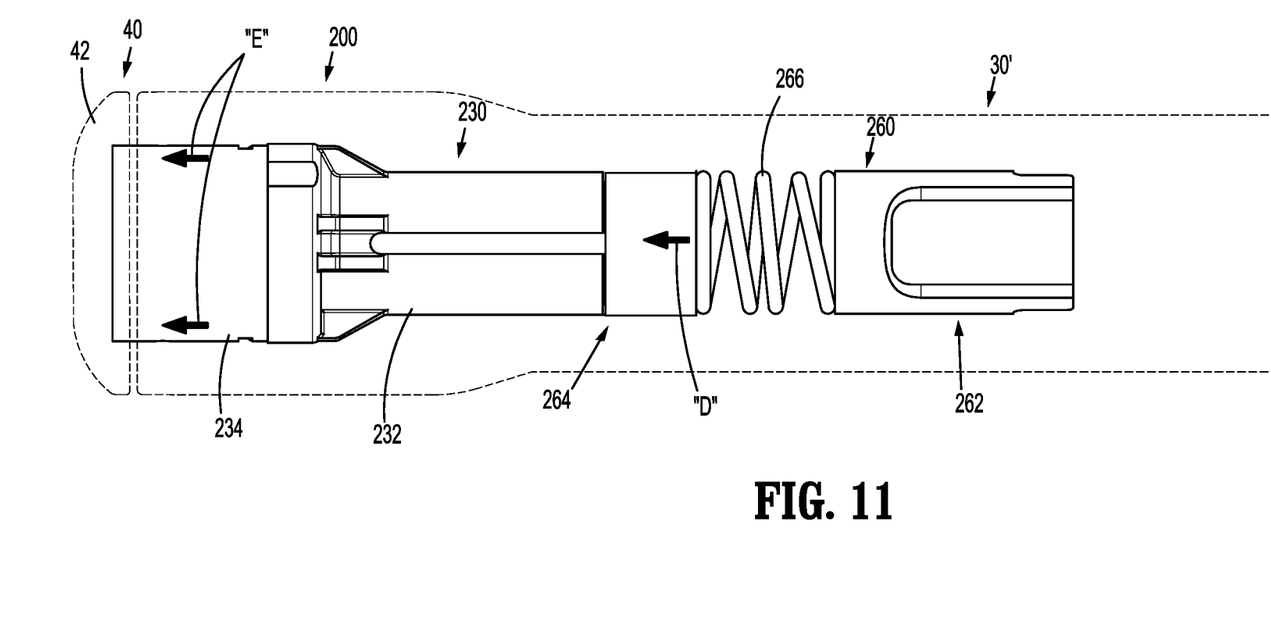
FIG. 11 is a side view of the knife assembly and the drive assembly of FIG. 7, with the knife assembly in an advanced position and the drive assembly in an activated position.

Turning to FIG. 11, once a force sufficient to break the connection, e.g., weld between the knife carrier 232 of the knife assembly 230 and the inner cylindrical portion 214 of the outer housing 210 is achieved, the knife carrier 232 separates from the inner cylindrical portion 214. The separation of the knife carrier 232 from the inner cylindrical portion 214 permits the release of the energy stored in the biasing member 266, causing instantaneous advancement of the distal drive section 264, as indicated by arrow "D". Advancement of the distal drive section 264 advances the attached knife assembly 230, as indicated by arrow "E", distally into the anvil member 42 of the anvil assembly 40.

By building energy in the biasing member 266, and then releasing the stored energy instantaneously, the knife 234 gains a velocity, and therefore, momentum to induce a higher force than that of the same force statically. This provides the knife assembly 230 with better cutting power to drive through staples and denser tissue in a cleaner manner and with less tissue trauma.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

The invention claimed is:

1. A circular stapling instrument comprising:
a handle assembly;
an elongate body extending from the handle assembly and including a drive member;
a cartridge assembly mounted on a distal end of the elongate body, the cartridge assembly including a knife assembly and an outer housing, the knife assembly being secured to the outer housing by a breakable connection, wherein the breakable connection is a weld; and
a drive assembly extending from the elongate body and operably disposed between the drive member and the knife assembly, the drive assembly including a proximal drive section, a distal drive section, and a biasing member disposed between the proximal and distal drive sections, wherein advancement of the proximal drive section a first distance compresses the biasing member, and advancement of the proximal drive section a second distance breaks the connection between the knife assembly and the outer housing.

2. The circular stapling instrument of claim 1, wherein the breakable connection maintains the knife assembly in a retracted position.

3. The circular stapling instrument of claim 1, wherein upon breaking of the breakable connection, the biasing member advances the distal drive section distally to advance the knife assembly.

4. The circular stapling instrument of claim 1, wherein compressing the biasing member stores energy in the biasing member.

5. The circular stapling instrument of claim 4, wherein the biasing member releases the stored energy when the breakable connection breaks.

6. The circular stapling instrument of claim 1, wherein the biasing member is a coil spring.

7. The circular stapling instrument of claim 1, wherein the knife assembly includes a knife carrier and a knife secured to the carrier, wherein the biasing member is disposed between the knife carrier of the knife assembly and the proximal drive section of the drive assembly.

8. The circular stapling instrument of claim 1, wherein the cartridge assembly is replaceable and selectively removably mounted on the distal end of the elongate body.

9. The circular stapling instrument of claim 1, wherein the breakable connection is a one-time breakable connection.

* * * * *